United States Patent [19]

Shackelford et al.

[11] Patent Number: 5,646,256
[45] Date of Patent: Jul. 8, 1997

[54] SATA AND OTHER THIOL PRECURSORS

[75] Inventors: William Shackelford, Towson, Md.; Josephine Readio, Sparta, N.J.; Samuel L. Moore, Owing Mills, Md.; Herman Rutner, Hackensack, N.J.

[73] Assignee: Becton, Dickinson and Company, Franklin Lakes, N.J.

[21] Appl. No.: 308,765

[22] Filed: Sep. 19, 1994

[51] Int. Cl.$^6$ .............. C07K 17/06; G01N 33/53; G01N 33/543

[52] U.S. Cl. .............. 530/391.1; 530/402; 436/533; 436/532

[58] Field of Search .............. 530/391.1, 402; 436/533, 532

[56] References Cited

U.S. PATENT DOCUMENTS 5,324,650  6/1994  Obzamsky et al. .............. 435/188

OTHER PUBLICATIONS

Neurochem. Res., Grossfeld et al., 1984, 9(7):947.

Duncan et al., Anal. Biochem., 1983, 132:68.

*Primary Examiner*—Frank C. Eisenschenk
*Attorney, Agent, or Firm*—Bruce S. Weintraub

[57] ABSTRACT

The present invention is directed to methods for using reagents to generate and stabilize thiols derived from thiol precursors in order to permit more effective reactions with thiol-reactive substances such as liposomes, proteins and antibodies. These methods provide greatly improved conjugates for utilization in various in vivo and in vitro applications.

12 Claims, 3 Drawing Sheets

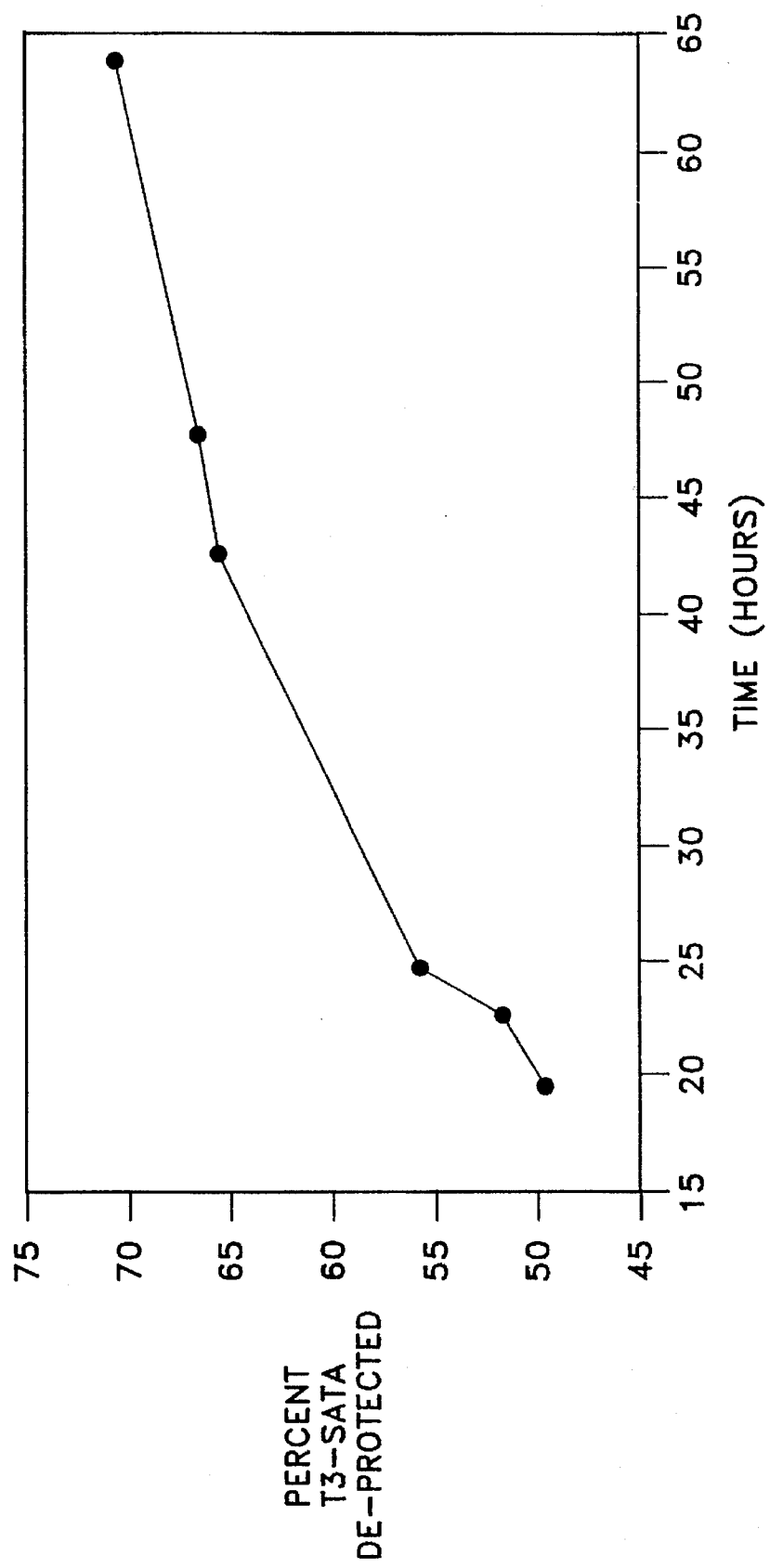

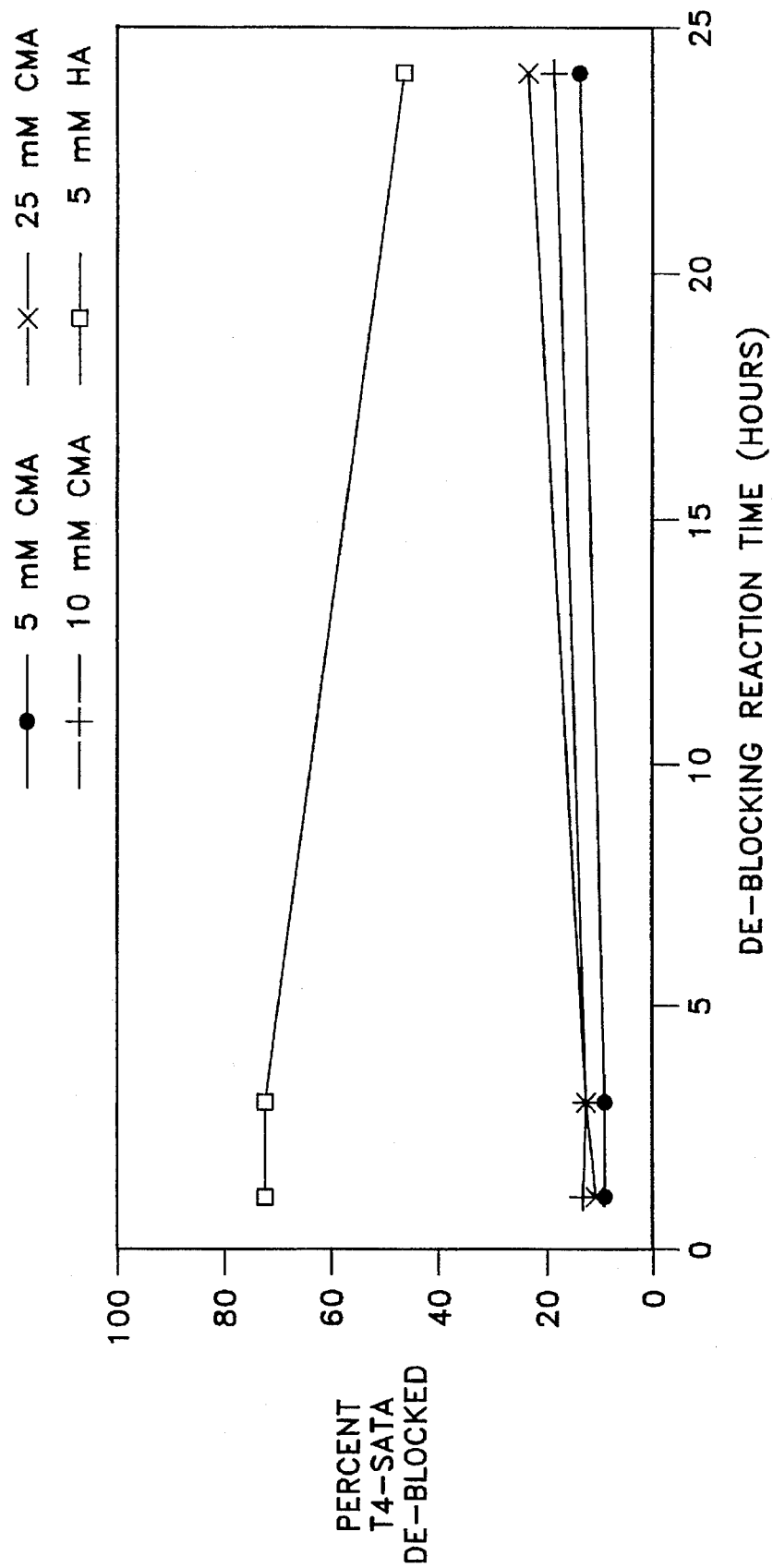

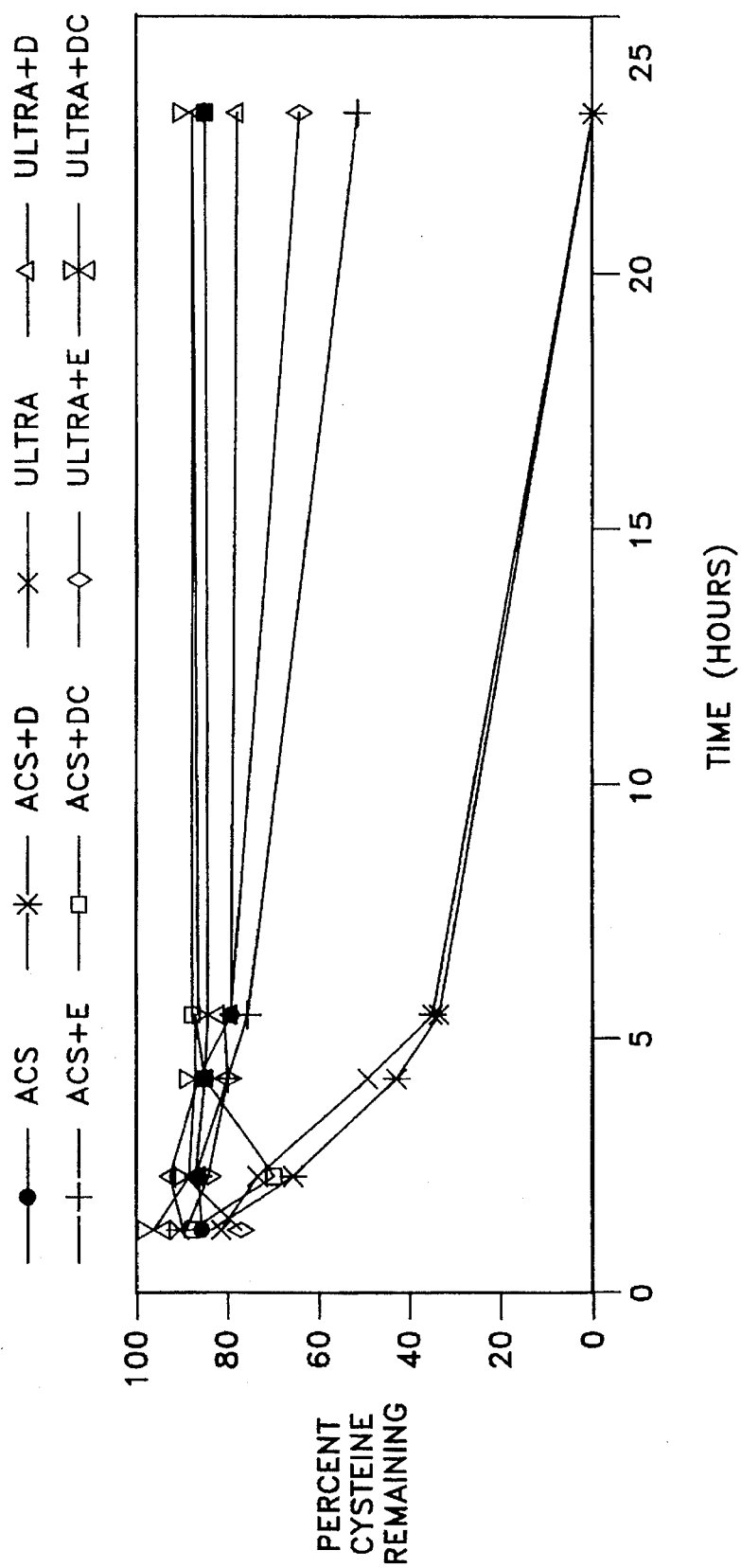

SATA AND OTHER THIOL PRECURSORS

FIELD OF THE INVENTION

The present invention relates to methods for utilizing reagents for generating and stabilizing thiols derived from S-acetyl and other thiol derivatives, permitting more selective and effective concurrent or sequential reactions with thiol-reactive substances (i.e., functionalized liposomes, proteins or antibodies) resulting in improved compositions or conjugates for in vitro and in vivo applications.

BACKGROUND OF THE INVENTION

Thiols, especially at pH above 6, are readily oxidized by oxygen or free radicals to nonreactive disulfides, a process that is known to be catalyzed by adventitious trace metal contaminants commonly found in reagents (particularly phosphates), buffers and even purified water. Hence, thiols are usually generated, prior to use, from protected precursors, such as S-acetylthioacetyl derivatives (Structure II below), prepared from N-succinimidyl-S-acetylthioacetyl (SATA) (Structure I, below), and conjugated immediately to thiol-reactive substances, e.g., maleimide or haloacetyl derivatives.

The conventional reagent for deblocking SATA derivatives is hydroxylamine (HA, Structure III) and for stabilization of thiols, the conventional chelating agent is ethylenediamine tetraacetic acid (EDTA). Deblocking and conjugation are done either concurrently (one-step) or sequentially (two-step). The advantage of HA over other deblocking agents of SATA is its rapid thiol generation at pH 7.5–8.0 and its relatively low competing side reaction with thiol-reactive reagents such as maleimide and haloacetyl derivatives. Hence, removal of the excess HA prior to conjugation is generally unnecessary.

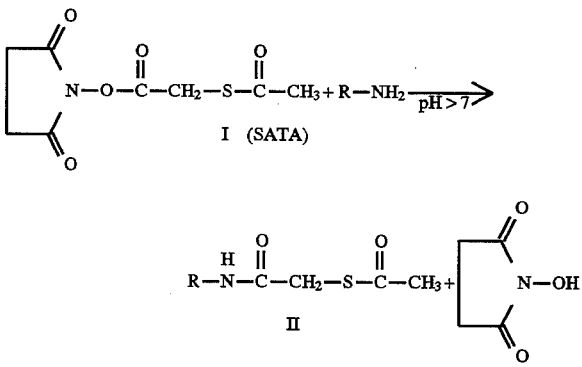

I (SATA)

Step 1: The reaction of SATA with a primary amine.

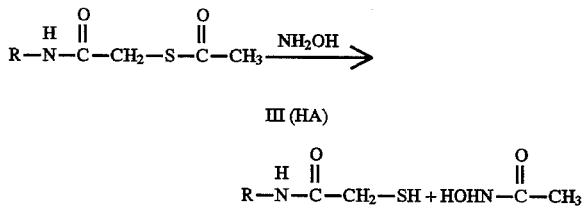

III (HA)

Step 2: Deprotection with hydroxylamine to generate the sulfhydryl.

However, the HA method was found to yield unstable antigen or antibody substituted liposomes.

The present invention describes a method for utilizing an alternative and less reactive reagent, carboxymethoxylamine (CMA), for generating thiols from SATA and SAMSA (S-acetylmercaptosuccinic anhydride) derivatives, as well as a superior chelant, diethylenetriamine pentaacetic acid (DTPA), for the protection of thiols during the deblocking and conjugation steps, which has yielded more stable and functionally superior liposomes.

The deblocking of SATA or SAMSA derivatives with carboxymethoxylamine by itself or in combination with EDTA or DTPA is a novel procedure described for the first time herein. The original publication regarding SATA by Duncan et al, Analyt. Biochem. 132: 68–73 (1983) used deblocking in pH 7.5 phosphate buffer, 1 mM EDT& for 1 hr at room temperature and sequential reaction with thiol-reactive protein derivatives for 24 hrs at 4° C. A review entitled "SATA" published in 1989 by PIERCE also uses EDTA chelation, however, no pertinent prior art is cited in this review.

BRIEF DESCRIPTION OF THE DRAWINGS

FIG. 1 is a graphic representation of the de-protection of T3-SATA by CMA over a 15–65 hour peeriod.

FIG. 2 is a graphic representation of the reaction time in hours for de-blocking of T4-SATA with CMA and HA over a 0–25 hour period.

FIG. 3 is a graphic representation of the instability of cysteine in the presence and absence of various chelating agents.

DETAILED DESCRIPTION OF THE INVENTION

The present invention relates to a method for utilizing a slower acting, but more effective reagent for generating thiols from SATA and other derivatives, CMA, and a superior chelant, DTPA. A derivative of HA, CMA (Structure IV a, b, c below), unlike HA, exists in nearly fully zwitterionic or anionic forms at pH 5–9.

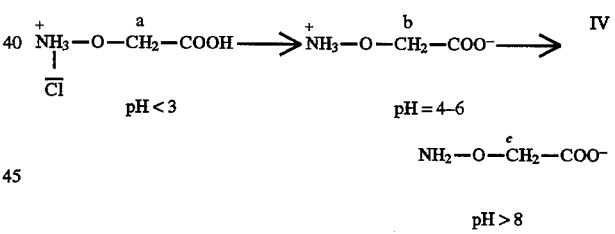

CMA was found to deblock SATA derivatives in the range of pH 7–10, and preferably at pH 7–8, albeit, at a slower rate than HA, due to the lower percentage of non-protonated amine in CMA in this pH range. Increasing the concentration of CMA ten to one-hundred fold provides more rapid deblocking rates comparable to HA. Additionally, thiol generation can be increased with time and thiol levels remain stable for more than 60 hrs. Faster deblocking occurs at higher pH but stability of thiols is reduced concomitantly. In comparison, the thiol concentration decreases to less than half in 24 hrs with the conventional HA/EDTA reagent. This is demonstrated by the results summarized in FIGS. 1 and 2.

The superior performance characteristics of CMA, when used in deblocking and conjugation with liposomes, are apparently due to the charged nature of CMA. This minimizes penetration and possible weakening of the hydrophobic liposome membrane, which is the probable cause of the higher leakage of the entrapped dye observed under stress/storage conditions when deblocking with HA. It is known that small uncharged molecules like $H_2O_2$ or HO—OH, which structurally resembles HA or $NH_2$—OH, readily penetrate liposome membranes and can react with labile membrane components.

Thus the attenuated reactivity of CMA is beneficial in concurrent deblock/conjugation reactions of proteins and with labile substrates where the lower nucleophilicity of CMA would result in fewer undesirable side reactions, such as cleavage of serine or threonine esters, or transaminations or deglycosylation, which may occur with HA.

Preferably, but not in anyway limiting the scope of the present invention, the thiol reactive substances which can be utilized herein can include haloacetyl or maleimide-substituted liposomes, latex, protein or antibody.

Conversely, the lower reactivity of CMA has necessitated longer deblocking reaction times in the one-step or two-step deblocking/conjugation modes and resulted in increased oxidation losses of the thiol even in the presence of EDTA to inhibit adventitious metal catalysts.

However, another chelant, DTPA, was found to be substantially more effective than EDTA in protecting thiols from oxidation to disulfides in the presence or absence of CMA. Such oxidations were found to occur even in buffers containing EDTA or treated with chelating resins (Chelex® 100) to inhibit or remove metal contaminants, respectively.

The presence of catalytic metal impurities in buffers was detected by the ascorbate oxidation assay of Buettner, *Methods in Enzymol.*, 186: 125–127 (1990), and by a slightly more sensitive cysteine oxidation method using Ellman's reagent as the chromogen.

In the concurrent deblocking/conjugation mode, the rate of thiol generation with CMA is considerably slower than the rate of reaction of thiol with the thiol-reactive reagent. Hence, the free thiol concentrations tend to be low and slower competing oxidation reactions are decreased. However, protection with DTPA is still found to be beneficial due to the apparently slower conjugations of thiols to maleimide on the surface of liposomes compared to soluble maleimide derivatives.

Another alternative deblocking mode for SATA and other S-acetyl derivatives, which contain no other alkali labile groups (e.g., T3, T4 and many other non-protein antigens), utilizes rapid to nearly instantaneous generation of thiols with 0.01 to 0.1M NaOH or other alkalis in the presence of DTPA and nitrogen to exclude oxygen (deblocking of SATA derivatives with 0.01M NaOH for ½ hr has been reported and probably results in considerable thiol oxidation even under exclusion of oxygen).

Upon completion of deblocking, the thiol is protected from oxidation and prepared for conjugation by addition of a weak acid (e.g., acetic acid) to adjust the pH to 6–8 prior to conjugation. Again, a highly effective chelant such as DTPA is needed, particularly during the high pH step, to minimize thiol oxidation.

In addition to faster deblocking and anticipated higher deblocking yields in alkali, this alternative NaOH procedure has the added advantages of flexibility in the choice of the conjugation pH for greater selectivity and non-reactivity of the neutralized deblocking reagent. This minimizes potential side reaction with the thiol-reactive group and other groups on the substrate which may occur with HA and even CMA.

The use of CMA/DTPA in lieu of the conventional HA/EDTA for deblocking SATA, SAMSA and other S-acetyl or S-acyl derivatives provides a means for more selective and milder deblockings/conjugations which are particularly desirable for liposome conjugations. The functionalities and stabilities of T3 and T4 liposomes prepared with CMA have proven superior to HA liposomes particularly after stress testing at 37° C. CMA, like HA, is commercially available as a stable HCl salt and can be converted to its active form by dissolution in a buffer of appropriate pH.

The CMA/DTPA combination was found to be superior to CMA/EDTA, HA/EDTA or HA/DTPA combinations. Deblocking of SATA or SAMSA derivatives with CMA/DTPA or with alkalis when permissible provides the additional advantages described herein.

In a preferred embodiment, DTPA chelant, rather than EDTA, can be used as a general thiol stabilizer and protectant in thiol reactions.

Another significant application of DTPA, direct thiolation of amino derivatives (i.e., proteins) via 2-iminothiolane (IT or Traut's Reagent which is described in *Pierce Reagents for Thiolation*), not requiring HA or CMA, involves concurrent functionalization of protein amino groups and thiol generation with one reagent in one step. This reaction is carded out in the pH range of 7–10, generally for several hours or overnight with or without EDTA present. There is a potential for significant losses of thiol through oxidation depending on the effectiveness of light/air exclusion and the absence of redox-active metallic contaminants in the buffers.

Generally, the iminothiolated protein is then purified by gel filtration prior to reaction with a thiol-reactive reagent in a subsequent step. In view of the demonstrated ability of DTPA, but not EDTA, to protect the thiol group of cysteine for 24–60 hrs, comparable protection will be expected for the iminothiolated product during the generation, purification and conjugation steps and thus significant improvements in conjugation efficiencies.

EXAMPLE I

Preparation of SATA-L-T4

Materials:

1. L-thyroxine, Sigma, Cat. No. T 2376

2. Dimethyl sulfoxide, Aldrich, Cat. No. 15,493-8.

3. SATA Sigma, Cat. No. A-9043

4. Acetic acid, ACS, any vendor

5. Triethylamine, 99%, Aldrich, Cat. No. 23,962-3

6. Chloroform, ACS, any vendor

7. Methanol, ACS, any vendor

8. TLC plates, Whatman, MK6F silica gel 60A, 1×3 inches, Cat. No. 4861-110

9. Pauly's reagent: store 3 components in refrigerator and mix before use:

a. 0.5% sulfanilic acid in 0.5M HCl b. 0.35% sodium nitrate in water c. 2.0M potassium carbonate in water Mix 5 mL a plus 5 mL b; let stand at room temperature for 2 min and add 10 mL c. Mix and use immediately. Spray dried TLC plates in the hood (wear gloves). Iodinated or unsubstituted phenols yield orange or red spots.

Procedure:
1. To a 20 mL glass vial with polycone screw cap, add:

| | | |
|---|---|---|
| L-T4 | 0.41 mmole | 320 mg |
| Dimethyl sulfoxide | | 2.0 mL |
| SATA | 0.77 mmole | 179 mg |

2. Stir briefly via magnetic stirrer to dissolve.
3. Add 120 uL (1.6 mmole) triethylamine
4. Cap and stir for 4 hrs. in the dark.
5. Add 0.6 mL acetic acid.
6. Add ice water/chips to fill the vial to 15 mL mark while stirring.
7. Stir for 5 min or until ice is melted.
8. Transfer to two 15 mL glass centrifuge tubes or 13×100 mm test tubes and centfifuge in tabletop centfifuge for 3 min at room temperature.
9. Aspirate the clear supernatants with a Pasteur piper.
10. Add 10 mL cold water per tube and resuspend the pellets with a small spatula.
11. Re-centrifuge.
12. Repeat steps 10 and 11 once more.
13. Aspirate the last supernatants (slightly turbid).
14. Dry the pellets in the tubes at room temperature/1–5 mm Hg vacuum overnight.
15. Transfer the dried pellets to a tared vial.
16. Crush the lumps with a spatula and continue drying for at least 6 hrs. at room temperature (or dry in myophilizer in step 14)
17. Yield: 0.32 g of of white powder of SATA-L-T4.
18. Purity: by TLC; Mk6F silica gel plates; system; chloroform-methanol-HOAc=8:2:0.2: 90% product at Rf0.75 (U.V., iodine, Pauly-positive), 5% at Rf0.9 (U.V. only; N, O-Storage; store at −15° to 20° C.

EXAMPLE Ia

Preparation of SATA-L-T3

This is analogous to the preparation of SATA-L-T4 in Example I.

EXAMPLE II

Deacetylation of Sata-L-T3 (and SATA-L-T4)

Reagents:
1. PBS: 0.05M phosphate, 0.075M sodium chloride, 1 mM DTPA pH 7.4.
2. CMA reagent (50 mM in PBS); 54.7 mg carboxymethoxylamine-HCl (Aldrich C1,340.8) in 10 mL PBS, pH 7.5.
3. Dimethyl sulfoxide, Aldrich#27,043-1.
4. SATA-L-T3 and SATA-L-T4: 100 mM=77 mg/mL DMSO and 89 mg/mL DMSO for SATA-T3 and SATA-T4, respectively.

Procedure:
1. SATA-L-T3 (or SATA-L-T4), 200 uL (20 umoles), was added slowly with stirring to 4.0 mL CMA reagent (200 umoles) and the mixture was stirred at room temperature in the dark for 24–65 hrs. in the presence of haloacetyl or maleimide derivatives.

EXAMPLE III

DE-BLOCKING of T3-SATA for IQ TT4 LIPOSOME PRODUCTION

A time course study of the de-blocking of the sulfhydryl group on the T3-SATA by CMA was undertaken. As FIG. 1 demonstrates, the percentage of T3-SATA de-blocked by 50 mM CMA (pH 7.4, 0.05M phosphate, 1.0 mM DTPA) increases gradually over time, and the de-blocking thiol groups are remarkably stable. This reaction with CMA is in sharp contrast to the de-blocking of T3-SATA with 5 mM HA, which peaks at around 70% in one hour and then degrades overnight to approximately 35% (data not shown).

At the time of the coupling (18–26 hours), the amount of T3-SATA that is de-blocked is slightly more than 50%. It appears from this experiment that this time window would yield 50–58% of the theoretical maximal T3-SATA de-blocking, and greater than 70% after 60 hours. The hours. The de-protected T3 thiol is very stable, due to the ultrapure chemical used to make the phosphate buffer (0.05M, pH 7.4), and more importantly, the presence of 1 mM DTPA in the buffer.

EXAMPLE IV

DE-BLOCKING of T4-SATA

FIG. 2 shows the effect of lower concentrations of CMA and of 5 mM HA on the deblocking rate of T4-SATA.

EXAMPLE V

INSTABILITY OF CYSTEINE

FIG. 3 shows the instability of cysteine in 0.05M phosphate, pH 7.4, in the absence and presence of 1 mM EDTA(E), 1 mM DTPA (D), and treatment with Chelex 100™(C). ACS and ULTRA denote buffers prepared from ACS and ultrapure grades of monosodium and disodium phosphates. The destruction of thiols with both grades of phosphate is partly inhibited by EDTA. As demonstrated in FIG. 3, DTPA is highly inhibitory, and chelation with Chelex® 100 provides yet a further increase in effectiveness.

What is claimed is:

1. A method of generating and stabilizing thiols from S-acetylated thiol derivatives, comprising:
   a) deblocking said derivative(s) with carboxymethoxy-lamine (CMA) in a pH range of 7–10 to generate the corresponding thiol; and
   b) stabilizing the thiol(s) from said thiol precursor.

2. A method of generating and stabilizing thiols, from S-acetylated thiol derivatives wherein said thiols, when conjugated concurrently or sequentially with thiol-reactive substances, result in a more stable conjugate, comprising:
   a) deblocking a thiol precursor with CMA in a pH range of 7–10;
   b) protecting thiol(s) generated from said thiol derivative with a chelating agent; and
   c) concurrently or sequentially reacting said generated thiol(s) with thiol-reactive substances.

3. A method of claim 2 wherein said chealating agent is ethylenediamine tetraacetic acid (EDTA).

4. A method of claim 2 wherein said chelating agent is diethylenetriamine pentaacetic acid (DTPA).

5. The method of claim 1 wherein CMA is in a pH range of 7–8.

6. The method of claim 2 wherein CMA is in a pH range of 7–8.

7. The method of claim 1 wherein said thiols are generated from thiolated derivatives selection from the group consisting of SATA derivatives, SAMSA derivatives, S-acetyl derivatives and S-acyl derivatives.

8. The method of claim 2 wherein said thiols are generated from S-acetyl derivatives selected from the group consisting of SATA derivatives, SAMSA derivatives, and other S-acetyl derivatives.

9. The method of claim 1 wherein the concentration of CMA is in the range of ten to one-hundred fold excess relative to the blocked thiol.

10. The method of claim 2 wherein the concentration of CMA is in the range of ten to one-hundred fold excess relative to the blocked thiol.

11. The method of claim 1 wherein said thiol-reactive substance is a haloacetyl or a maleimido-substituted liposome, latex, protein or antibody.

12. The method of claim 2 wherein said thiol-reactive substance is a haloacetyl or a maleimido-substituted liposome, latex, protein or antibody.

* * * * *